United States Patent [19]
Aoyama et al.

[11] Patent Number: 5,177,274
[45] Date of Patent: Jan. 5, 1993

[54] PROCESS FOR PREPARING PENTAFLUORODICHLOROPROPANES

[75] Inventors: Hirokazu Aoyama; Satoru Kono; Satoshi Koyama, all of Osaka, Japan

[73] Assignee: Daikin Industries Ltd., Osaka, Japan

[21] Appl. No.: 743,686

[22] Filed: Aug. 12, 1991

Related U.S. Application Data

[63] Continuation-in-part of Ser. No. 636,582, Jan. 2, 1991, abandoned.

[30] Foreign Application Priority Data

Jan. 8, 1990 [JP] Japan ............ 2-1314
Mar. 3, 1990 [JP] Japan ............ 2-52362

[51] Int. Cl.$^5$ ............ C07C 17/26
[52] U.S. Cl. ............ 570/172
[58] Field of Search ............ 570/172

[56] References Cited

U.S. PATENT DOCUMENTS 3,310,589  3/1967  Ketley ............ 570/172

OTHER PUBLICATIONS

Coffman et al., J. Amer. Chem. Soc. 71, 979–980.

Primary Examiner—Alan Siegel
Attorney, Agent, or Firm—Birch, Stewart, Kolasch & Birch

[57] ABSTRACT

1,1,1,2,2-Pentafluoro-3,3-dichloropropane and 1,1,2,2,3-pentafluoro-1,3-dichloropropane are prepared by reacting dichlorofluoromethane and tetrafluoroethylene in a solvent in the presence of a catalyst with improved conversion and selectivity.

13 Claims, No Drawings

PROCESS FOR PREPARING PENTAFLUORODICHLOROPROPANES

This application is a continuation-in-part of application Ser. No. 07/636,582 filed on Jan. 2, 1991, now abandoned, the entire contents of which are hereby incorporated by reference.

BACKGROUND OF THE INVENTION

1. Field of the Invention

The present invention relates to a process for preparing pentafluorodichloropropanes. More particularly, the present invention relates to a process for preparing 1,1,1,2,2-pentafluoro-3,3-dichloropropane (hereinafter referred to as "R-225ca") and 1,1,2,2,3-pentafluoro-1,3-dichloropropane (hereinafter referred to as "R-225cb") which are promising substitute compounds for industrially important 1,1,2-trichloro-1,2,2-trifluoroethane and have less influence on global environments.

2. Description of the Related Art

Hitherto, R-225ca and R-225cb have been industrially prepared by reacting tetrafluoroethylene (hereinafter referred to as "TFE") and dichlorofluoromethane (hereinafter referred to as "R-21") in the presence of a catalyst such as anhydrous aluminum chloride at a temperature of from 15 to 100° C. (see J. Amer. Chem. Soc., 71, 979) and Collec. Czechoslov. Chem. Commun., 36, 1867). In addition, R-225ca is prepared by reacting TFE with cesium fluoride in diglyme and then with chloroform (see U.S. Pat. No. 3,381,042).

However, since the above first process reacts the starting materials batchwise in an autoclave or a glass reactor at a temperature of from 15 to 100° C., a selectivity and yield of the desired product is low, for example, the yield is from 46 to 58 % so that this process is industrially uneconomical. In addition, to separate the catalyst from the product after the reaction, the product is collected with a cooled trap under reduced pressure, or the catalyst is treated with dilute hydrochloric acid and then the product is recovered.

In the above second process utilizing cesium fluoride, though the selectivity and the yield of the desired product are good, cesium fluoride which is one of the starting materials is very expensive, so that this process is entirely unsuitable for preparing the desired product industrially.

SUMMARY OF THE INVENTION

An object of the present invention is to provide a process for preparing R-225ca and R-225cb with improved selectivity and yield.

According to the present invention, there is provided a process for preparing R-225ca and R-225cb comprising reacting R-21 and TFE in a solvent in the presence of a catalyst.

DETAILED DESCRIPTION OF THE INVENTION

In the process of the present invention, when anhydrous aluminum chloride is used as a catalyst and R-225ca or R-225cb or a mixture of them is used as a solvent, a predetermined amount of anhydrous aluminum chloride is suspended in the solvent, and then R-21 and TFE are bubbled in the solvent in a predetermined molar ratio at a predetermined flow rate. As the reaction proceeds, a reaction mixture containing produced R-225ca and R-225cb is recovered from the reactor and R-225ca and R-225cb are separated from the catalyst. To separate R-225ca and R-225cb from the catalyst, any conventional methods such as filtration in a liquid state or distillation in a gas state can be used. The recovered reaction mixture is purified by conventional methods such as rectification to obtain desired R-225ca and R-225cb.

In the process of the present invention, preferably the raw materials are continuously fed and the products are continuously recovered in view of production cost. Alternatively, a semi-batchwise system can be used, in which the raw materials are continuously fed, the reaction is carried out for a certain time without feeding the raw materials and then the products are recovered.

As the catalyst, any catalyst which has catalytic activity on the addition reaction of R-21 to TFE may be used. In particular, Lewis acids such as anhydrous aluminum chloride, anhydrous titanium tetrachloride, anhydrous tin tetrachloride, anhydrous antimony pentachloride, anhydrous zinc chloride, anhydrous iron chloride, anhydrous aluminum bromide and boron trifluoride are preferred. Further, a catalyst of the composition formula:

$$AlCl_xF_yO_z \qquad (I)$$

wherein x, y and z are numbers which satisfy $x + y + 2z = 3, 0 < x < 3, 0 \leq y < 3$ and $0 \leq z < 3/2$ provided that at least one of y and z is not 0 (zero), for example, aluminum chlorofluoride or alumina chlorofluoride can be used.

Aluminum chlorofluoride to be used as the catalyst in the process of the present invention may be prepared by reacting hydrogen fluoride, hydrofluoric acid or a fluoroor chlorofluoro-hydrocarbon having not more than 4 carbon atoms, preferably not more than 2 carbon atoms with aluminum chloride. Examples of the fluoro- or clhlorofluoro-hydrocarbon are trifluoromethane, tetrafluoroethane, chlorodifluoromethane, dichlorofluoromethane, trifluorodichloroethane, trifluorochloromethane, difluorotetrachloroethane, trifluorotrichloroethane and the like. In this reaction, hydrogen fluoride, hydrochloric acid or the fluoro- or chlorofluoro-hydrocarbon may be used independently or as a mixture of two or more of them. In some cases, chlorohydrocarbon may be used together with them. The reaction temperature is from 0 to 120° C., preferably from 0 to 100° C. The fluorine source material can be reacted with the aluminum chloride in a liquid state or gas state.

Alumina chlorofluoride to be used as the catalyst in the process of the present invention may be prepared by reacting chlorohydrocarbon, chlorofluorohydrocarbon, fluorohydrocarbon, hydrogen chloride or a mixture thereof with activated alumina at a temperature of from 100° to 700° C. Usually, this preparation process comprises filling alumina in a reactor made of stainless steel, Hasteloy or glass, heating alumina at a temperature of from 300° to 500° C. in a stream of dry nitrogen to dry alumina thoroughly, and then flowing the halogenated hydrocarbon alone or a mixture of the halogenated hydrocarbon and hydrogen chloride gas or oxygen at a suitable temperature, for example, from 100° to 600° C., preferably from 200° to 400° C. for a predetermined period of time. When the reaction temperature is lower than 100° C., the reaction time becomes unpractically long. When the reaction temperature is higher than 600° C., carbon is deposed on the aluminum particle surfaces so that the catalytic activity tends to be deteriorated. Deactivation caused by the deposited carbon can be prevented by the presence of oxygen or the air as disclosed in Japanese Parent Publication No. 27375/1986.

The treatment with hydrogen chloride gas can be carried out in the similar manner. Namely, activated alumina is thoroughly dried at a temperature of 400° to 800° C. in a stream of dry nitrogen. Then, hydrogen chloride gas as such or diluted with an inert gas (e.g. nitrogen or argon) or chlorofluorohydrocarbon (e.g. dichlorodifluoromethane (R-12) or R-21) is flowed over dried alumina. The flowing time is usually from 3 to 10 hours.

As alumina, commercially available porous alumina which comprises γ-alumina and is used for dehydration or as a catalyst may be used. For example, "Neobead" C, MHR, GB and D (manufactured by Mizusawa Chemical Industries, Ltd.) or activated alumina KHA and NKH (manufactured by Sumitomo Chemical Co., Ltd.) can be used.

As chlorohydrocarbon or chlorofluorohydrocarbon having no hydrogen, those having 1, 2 or 3 carbon atoms, preferably 1 or 2 carbon atoms are used. Preferred examples are carbon tetrachloride, fluorotrichloromethane, difluorodichloromethane, trifluorochloromethane, 1,1,2-trichloro1,2,2-trifluoroethane, 1,1,1-trichloro-2,2,2-trifluoroethane, 1,1,2,2-tetrafluoro-1,2-dichloroethane, 1,1,1,2-tetrafluoro-2,2-dichloroethane, 1,1,2,2-tetrachloro-1,2-difluoroethane, 1,1,1,2-tetrachloro-2,2-difluoroethane and the like. As chlorohydrocarbon or chlorofluorohydrocarbon having at least one hydrogen, those having 1, 2 or 3 carbon atoms, preferably 1 or 2 carbon atoms are used. Preferred examples are fluorodichloromethane, difluorochloromethane, 1,1,1-trifluoro-2,2-dichloroethane, 1,1,2-trifluoro-1,2-dichloroethane, 1,1,1-trifluoro-2-chloroethane and the like.

The alumina chlorofluoride catalyst may be prepared by reacting alumina with an inorganic fluoride, for example, with hydrogen fluoride at a temperature of from 20 to 450° C., with sulfur fluoride (e.g. $SF_4$ or $SF_6$), sulfuryl fluoride or thionyl fluoride at a temperature of from 300 to 500° C., or with ammonium fluoride (e.g. acidic ammonium fluoride or neutral ammonium fluoride) at a temperature of from 20° to 450° C., and then with chlorofluorohydrocarbon, chlorohydrocarbon or hydrogen chloride.

The above catalysts may be used independently or as a mixture of two or more of them.

Among the catalysts, anhydrous aluminum chloride and the catalyst having the above composition formula (I) are particularly preferred.

As the solvent, any solvent that is inactive to the catalyst and in that R-21 and TFE are dissolved can be used. However, chloroalkanes other than chloromethane and dichloromethane, and chlorofluoroalkane having one carbon atom are not preferred since they will greatly decreases a selectivity of R-225.

Preferred examples of the solvent are chloromethane, dichloromethane and chlorofluoro- or hydrochlorofluoro-alkanes having at least two carbon atoms, in particular 2 to 10 carbon atoms. Specific examples of the solvent are trichlorotrifluoroethane, dichlorotrifluoroethane, chlorotrifluoroethane, dichlorotetrafluoroethane, chlorotetrafluoroethane, tetrachlorotetrafluoropropane, trichlorotetrafluoropropane, dichlorotetrafluoropropane, chlorotetrafluoropropane, trichloropentafluoropropane, dichloropentafluoropropane, chloropentafluoropropane, and perfluoroalkanes such as perfluorohexane, perfluorooctance and perfluorodecane, etc. In view of separation of the desired products R-225ca and R-225cb, R-225ca and R-225cb are preferably used as the solvents.

An amount of the catalyst in the solvent is selected so that the weight of the solvent is at least two time the weight of the catalyst. When the solvent weight is less than this lower limit, the reaction system cannot be effectively stirred, and the selectivity of R-225 tends to be low in an initial stage of the reaction.

A molar ratio of R-21 to TFE is at least 1:1, preferably from 1:1 to 1:10. When the molar ratio is less than 1:1, unreacted R-21 is accumulated in the reaction system and catalyzed by the catalyst such as anhydrous aluminum chloride to provide R-22 (difluorochloromethane), R-23 (trifluoromethane) or chloroform in a larger amount.

The raw materials can be charged in the reaction system by any suitable method. For example, R-21 and TFE are mixed and then charged, or R-21 and TFE are independently charged at the same time. Alternatively, R-21 is charged for a certain period of time and then TFE is charged for a certain period of time.

When the molar ratio of R-21 to TFE is 1:1, the selectivity is slightly decreased. In this case, the decrease of selectivity is prevented by dissolving TFE in the solvent before the start of reaction. When the molar ratio of R-21 to TFE is larger than 1:1, there is no substantial difference in the selectivity and the conversion. As the ratio of TFE is increased, the amount of TFE to be recycled increases. Therefore, the upper limit of the molar ratio is preferably about 1:10.

R-21 and TFE may be charged in the gas state or the liquid state.

In the conventional method such as the batchwise process in the liquid phase utilizing anhydrous aluminum chloride, the selectivity of R-225 is very low since the unreacted R-21 is accumulated in the reaction system. However, the high selectivity of R-225 is achieved by controlling the concentration of R-21 in the reaction system to 3% by weight or less, preferably to 1% by weight or less by using the solvent during the course of reaction. Preferably, the concentration of R-21 in the reaction system is not smaller than 0.001 % by weight. Herein, the reaction system means a mixture of the reactants, the solvent and the products.

Reaction pressure is not critical and may be reduced pressure. However, since a complicated reaction apparatus should be used in case of the reduced pressure, the reaction is preferably carried out at or above the atmospheric pressure.

A reaction temperature in the process of the present invention is from −30° to +120° C., preferably from −20° to +60° C. When the reaction temperature is higher than 120° C., the amounts of the by-products increase, and the selectivity of desired R-225ca and R-225cb decreases. When the reaction temperature is lower than −30° C., the reaction rate becomes unpractically low.

R-21 and TFE which are used as the starting materials in the process of the present invention are commercially produced. The Lewis acids such as anhydrous aluminum chloride can be commercially available ones.

PREFERRED EMBODIMENTS OF THE INVENTION

The present invention will be illustrated by following Examples.

EXAMPLE 1

In a 100 ml reactor equipped with an ice-cooled condenser an outlet of which was connected with a trap kept at −70° C., R-225ca (20 g) and ground anhydrous aluminum chloride (1 g) were charged. After stirring the mixture to suspend anhydrous aluminum chloride in R-225ca, premixed R-21 and TFE were introduced in the suspension at flow rates of 10 ml/min. and 30 ml/min., respectively to initiate the reaction. After 30 minutes from the initiation of the reaction, the temperature of the reaction mixture reached 40° C. After supplying R-21 and TFE for 4 hours, their supply was terminated, and aluminum chloride was removed from the solution in the reactor by filtration. The filtrate was analyzed by gas chromatography. A liquid trapped in the trap kept at −70° C. was analyzed in the same manner. The results are shown in Table 1.

TABLE 1

| Composition (%) by gas chromatography | Reaction solution | Trapped liquid |
|---|---|---|
| TFE | 0.9 | 1.2 |
| R-22 | 0 | 0.1 |
| R-21 | 0.1 | 3.8 |
| R-225ca + R-225cb | 94.5 | 91.1 |
| CHCl$_3$ | 2.0 | 3.1 |
| R-224*[1] | 2.5 | 0.5 |
| Total weight (g) | 33.5 | 5.7 |

Note:
*[1]Tetrafluorodichloropropane.

From the above content of R-225ca and R-225cb, the weight of initially charged R-225ca was subtracted, and the conversion of R-21 was calculated to be 98 % by mole and the selectivity of R-225 was calculated to be 91 % by mole. Produced R-225 was a mixture of R-225ca and R-225cb in a molar ratio of 52:48 (R-225ca:R-225cb).

EXAMPLE 2

In the same reactor as used in Example 1, R-225ca (20 g) and anhydrous aluminum chloride (1 g) were charged. While the mixture was stirred and cooled with iced water from outside, TFE was flowed in the reaction mixture at a flow rate of 10 ml/min for 10 minutes. Thereafter, premixed R-21 and TFE were introduced in the reaction mixture at flow rates of 10 ml/min. and 10 ml/min., respectively at 3° C. to initiate the reaction. After 30 minutes from the initiation of the reaction, the temperature of the reaction mixture reached 7° C. After supplying R-21 and TFE for 6 hours, their supply was terminated. No liquid was trapped in the trap kept at −70° C.

The product was analyzed in the same manner as in Example 1 to find that the conversion of R-21 was 99% by mole and the selectivity of R-225 was 94% by mole. The amount of produced R-225 was 28.2 g. Produced R-225 was a mixture of R-225ca and R-225cb in a molar ratio of 52:48 (R-225ca:R-225cb)

EXAMPLE 3

This Example shows a reaction in which the reaction mixture is continuously withdrawn from the reactor.

The same reactor as used in Example 1 was used, but an outlet having a glass filter for withdrawing a liquid from the reactor was equipped and further a cooling jacked was provided to control the temperature in the reactor.

In the above reactor, a mixture of R-225ca and R-225cb in a molar ratio of 50:50 (200 g) and ground anhydrous aluminum chloride (10 g) were charged, and TFE was flowed at a flow rate of 10 ml/min. for 10 minutes at a liquid temperature of 5° C. while stirring. Then, premixed R-21 and TFE were introduced in the liquid at flow rates of 100 ml/min. and 10 ml/min., respectively to initiate the reaction. A molar ratio of R-21 to TFE was 1:1. The cooling temperature was controlled so that the liquid temperature did not exceed 5° C. After 30 minutes from the initiation of the reaction, the liquid was withdrawn through the outlet having the glass filter at a rate of 54 g/hr., and the reaction was continued for 30 hours in total. After terminating the reaction, the reaction mixture remained in the reactor was recovered by filtration and combined with the already withdrawn liquid. The combined liquid was rectified to obtain a mixture of R-225ca and R-225cb in a molar ratio of 48:52 (1360 g). Since an amount of simultaneously recovered R-21 was 38 g, the conversion of R-21 was 95 %, and the selectivity of R-225 was 94%.

EXAMPLE 4

In a 100 ml stainless steel autoclave, anhydrous aluminum chloride (1 g) and a mixture of R-225ca and R-225cb in a molar ratio of 52:48 (20 g) were charged. A still portion of the autoclave was cooled at −40° C., and R-21 and TFE were flowed at flow rates of 10 ml/min. and 10 ml/min., respectively for 2 hours. Thereafter, the reaction was terminated and the content in the autoclave was withdrawn and analyzed by gas chromatography. The conversion and the selectivity are shown in Table 2.

EXAMPLE 5

In the same manner as in Example 4 but heating the still portion of the autoclave at 60° C., the reaction was carried out. The results are shown in Table 2.

EXAMPLE 6

In the same manner as in Example 4 but heating the still portion of the autoclave at 120° C, the reaction was carried out. The results are shown in Table 2.

TABLE 2

| Example No. | Conversion of R-21 (mol. %) | Selectivity of R-225ca (mol. %) |
|---|---|---|
| 4 | 5 | 95 |
| 5 | 100 | 82 |
| 6 | 100 | 55 |

EXAMPLE 7

In a three-necked 100 ml flask, alumina chlorofluoride (10 g) and a mixture of R-225ca and R-225cb in a molar ratio of 52:48 (20 g) were charged. In the mixture, premixed R-21 and TFE were introduced in the suspension at flow rates of 10 ml/min. and 30 ml/min., respectively to initiate the reaction. After 3 hours, the reaction liquid in the flask and the trapped liquid were combined and analyzed by gas chromatography. The conversion of R-21 was 98% by mole and the selectivity of R-225 was 95% by mole.

Alumina chlorofluoride used in this Example was prepared as follows:

In a SUS 316 reactor tube having an inner diameter of 20 mm, Neobead GB (40 ml) was filled and dried at 400° C. in a stream of dry nitrogen for 6 hours. Then, the interior temperature was lowered to 300° C. and the supply of nitrogen was stopped. Then, R-21 was flowed in the reactor tube till the amount of exited carbon dioxide did not decrease in gas chromatographic analysis. Thereafter, the reactor tube was cooled to 30° C. and the catalyst was recovered.

The composition of the catalyst was analyzed according to the thermohydrolysis disclosed by P. Woodbridge et al, Nature, 229, 626 (1971). The result is as follow:

Al: 45.5% by weight
Cl: 2.3% by weight
F: 20.1% by weight
O: 32.1% by weight

EXAMPLE 8

In a three-necked 100 ml flask, anhydrous aluminum chloride (1 g) and dichloromethane (20 g) were charged. While cooling the flask with ice, premixed R-21 and TFE were introduced in the flask at flow rates of 10 ml/min. and 30 ml/min., respectively to initiate the reaction. After 3 hours, the reaction liquid in the flask and the trapped liquid were combined and analyzed by gas chromatography. The conversion of R-21 was 98% by mole and the selectivity of R-225 was 70% by mole.

EXAMPLE 9

In a three-necked 100 ml flask, aluminum chlorofluoride (1 g) and a mixture of R-225ca and R-225cb in a molar ratio of 52:48 (20 g) were charged. While cooling the flask with ice, premixed R-21 and TFE were introduced in the flask at flow rates of 10 ml/min. and 12 ml/min., respectively to initiate the reaction. After 3 hours, the reaction liquid in the flask and the trapped liquid were combined and analyzed by gas chromatography. The conversion of R-21 was 99% by mole and the selectivity of R-225 was 96% by mole.

Aluminum chlorofluoride used in this Example was prepared as follows:

In a glass reactor tube having an inner diameter of 10 mm, anhydrous aluminum chloride (2.5 g) was filled and R-21 was flowed in the reactor tube at a flow rate of 10 ml/min. for 1 hour. Then, the catalyst was recovered and used in the above reaction.

The composition of the catalyst was analyzed by dissolving aluminum chlorofluoride (10 mg) in pure water (1 liter) and measuring amounts of F and Cl with ion chromatography. The result is as follow:

Al: 25% by weight
Cl: 59% by weight
F: 16% by weight

EXAMPLE 10

In a three-necked 100 ml flask, anhydrous aluminum chloride (0.5 g) and R-214 (tetrachlorotetrafluoropropane) (20 g) were charged. While cooling the flask with ice, premixed R-21 and TFE were introduced in the flask at flow rates of 10 ml/min. and 12 ml/min., respectively to initiate the reaction. After 3 hours, the reaction liquid in the flask and the trapped liquid were combined and analyzed by gas chromatography. The conversion of R-21 was 99% by mole and the selectivity of R-225 was 92% by mole.

EXAMPLE 11

In a three-necked 100 ml flask, anhydrous aluminum chloride (0.5 g) and R-224 (trichlorotetrafluoropropane) (20 g) were charged. With cooling the flask with ice, premixed R-21 and TFE were introduced in the flask at flow rates of 10 ml/min. and 12 ml/min., respectively to initiate the reaction. After 3 hours, the reaction liquid in the flask and the trapped liquid were combined and analyzed by gas chromatography. The conversion of R-21 was 99% by mole and the selectivity of R-225 was 91% by mole.

COMPARATIVE EXAMPLE

In a silver-lined autoclave, anhydrous aluminum chloride (5 g) was charged. After the autoclave was cooled in a dry ice/acetone bath and evacuated, R-21 (52 g, 0.5 mole) and TFE (50 g, 0.5 mole) were charged by evaporation through a cylinder. The autoclave was closed and heated at 100° C. for 10 hours while stirring the content. Then, the autoclave was opened, and the reaction mixture was recovered and washed with dilute hydrochloric acid to obtain a mixture of R-225ca and R-225cb (47 g, 0.23 mole). The yield was 46.3 % based on R-21. According to gas chromatographic analysis of the product, the conversion of R-21 was 98.0% by mole and the selectivity of R-225 was 48% by mole.

What is claimed is:

1. A process for preparing 1,1,1-2,2-pentafluoro3,3-dichloropropane and 1,1,2,2,3-pentafluoro-1,3-dichloropropane comprising reacting in a reaction system dichlorofluoromethane and tetrafluoroethylene in a solvent in the presence of a Lewis acid catalyst, wherein a concentration of dichlorofluoromethane is not higher than 3% based on a total weight of the reaction system.

2. The process according to claim 1, wherein said catalyst is anhydrous aluminum chloride.

3. The process according to claim 1, wherein said catalyst is a compound of the composition formula:

$$AlCl_xF_yO_z \qquad (I)$$

wherein x, y and z are numbers which satisfy $x + y + 2z = 3$, $0 < x < 3$, $0 \leq y < 3$ and $0 \leq z < 3/2$ provided that at least one of y and z is not 0 (zero).

4. The process according to claim 1, wherein said solvent is at least one member selected from the group consisting of chloromethane, dichloromethane and chlorofluoroalkane having at least two carbon atoms.

5. The process according to claim 1, wherein said solvent is a hydrochlorofluoroalkane having at least two carbon atoms.

6. The process according to claim 1, wherein said solvent is pentafluorodichloropropane.

7. The process according to claim 1, wherein said solvent is at least one member selected from the group consisting of 1,1,1,2,2-pentafluoro-3,3-dichloropropane and 1,1,2,2,3-pentafluoro-1,3-dichloropropane.

8. The process according to claim 1, wherein said solvent is trichlorotetrafluoropropane.

9. The process according to claim 1, wherein a reaction temperature is from −30° to 120° C.

10. The process according to claim 1, wherein a concentration of fluorodichloromethane in a reaction liquid is kept at 1% by weight or less.

11. The process according to claim 1, wherein fluorodichloromethane and tetrafluoroethane are continuously supplied to a reaction system.

12. The process according to claim 1, wherein fluorodichloromethane and tetrafluoroethane are continuously or discontinuously supplied in such a ratio that at least one mole of tetrafluoroethylene is supplied per one mole of fluorodichloromethane.

13. The process according to claim 1, wherein the produced 1,1,1,2,2-pentafluoro-3,3-dichloropropane and 1,1,2,2,3-pentafluoro-1,3-dichloropropane are continuously or discontinuously withdrawn from the reaction system.

* * * * *